United States Patent [19]
Evans, Sr.

[11] 4,404,968
[45] Sep. 20, 1983

[54] PUMP AND VALVE ASSEMBLY FOR PENILE IMPLANT

[76] Inventor: Alvin S. Evans, Sr., 234 Shubert Ave., Runnemede, N.J. 08078

[21] Appl. No.: 366,447

[22] Filed: Apr. 7, 1982

[51] Int. Cl.³ .............................................. A61F 5/00
[52] U.S. Cl. .............................................. 128/79; 3/1
[58] Field of Search ................. 128/1 R, 79, DIG. 25; 3/1

[56] References Cited

U.S. PATENT DOCUMENTS

| | | | |
|---|---|---|---|
| 3,954,102 | 5/1976 | Buuck | 128/79 |
| 4,364,379 | 12/1982 | Finney | 128/79 |
| 4,369,771 | 1/1983 | Trick | 128/79 |

OTHER PUBLICATIONS

Kothari et al., "An Implantable Fluid Transfer System for Treatment of Impotence" Jo. Biomechanics 1972, vol. 5, pp. 567-570, (Pergamon Press).

*Primary Examiner*—Dalton L. Truluck
*Attorney, Agent, or Firm*—Caesar, Rivise, Bernstein & Cohen, Ltd.

[57] ABSTRACT

For simulating a natural erection, a pump and valve assembly to be used in combination with a prosthetic penile implant which includes bladder means which are implanted within the penis and a fluid containing reservoir which is implanted within the abdominal cavity. The pump and valve assembly is generally implanted within the scrotum. To that end, the pump and valve assembly includes a rotor and uni-directional valve means such that the fluid is able to flow from the reservoir to the bladders when the rotor is in a first position and from the bladders to the reservoir when the rotor is in a second position. To that end, the valve means precludes the fluid from flowing in the reverse direction once the fluid has passed to either the reservoir or the bladders, respectively. Moreover, pump means are utilized in order to pump additional fluid either into the bladders to obtain a fully erect penis or alternatively, to pump fluid out of the bladders and into the reservoir to obtain a flaccid penis. In one embodiment of the invention, the rotor is manually rotated by actuating a slide lever comprising a portion of the assembly which is implanted with the scrotum. In another embodiment of the invention the valve assembly is implanted within the abdominal cavity while the primary inflation pump as well as a pair of volumetrically small actuator pumps are implanted within the scrotum and arranged such that by squeezing the actuator pumps, either an extension or a contraction of bellows occurs, resulting in corresponding rotation of the rotor.

20 Claims, 10 Drawing Figures

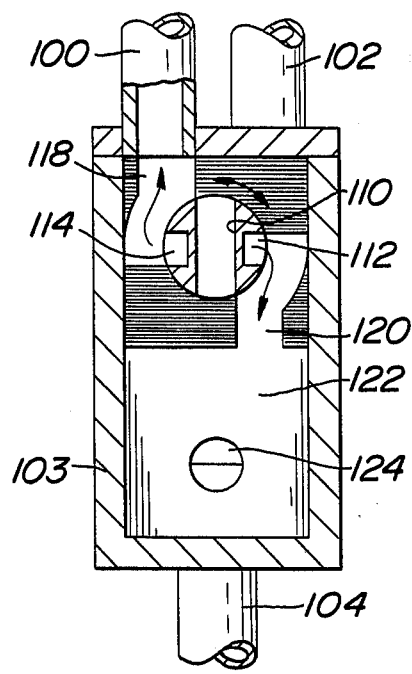
FIG. 2A
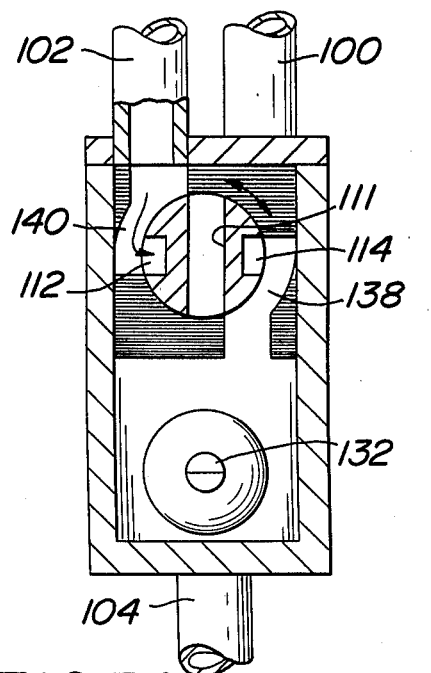
FIG. 3A
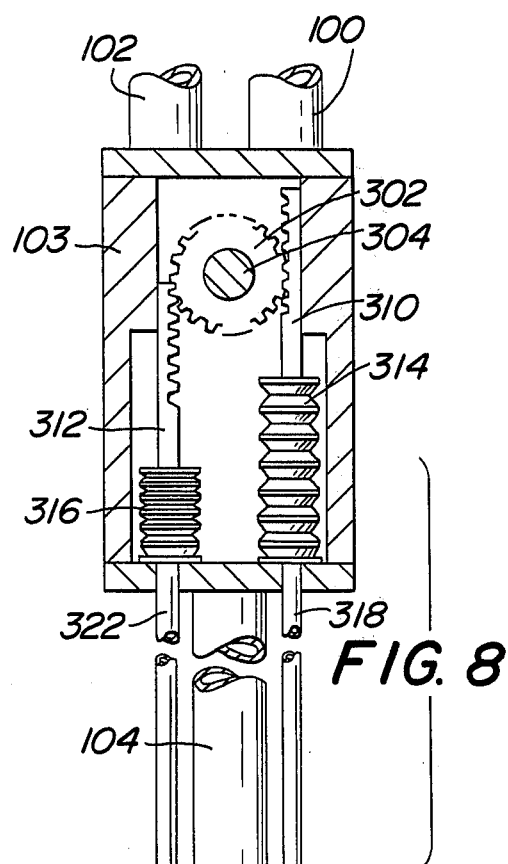
FIG. 8
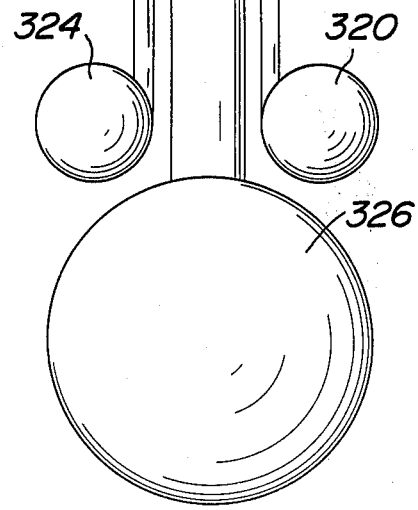

PUMP AND VALVE ASSEMBLY FOR PENILE IMPLANT

BACKGROUND OF THE INVENTION

This invention relates generally to prosthetic devices and more particularly to a pump and valve assembly for use in combination with a penile implant device.

In order to remedy the effects of certain types of functional impotency, implants have been developed for surgical insertion in a penis in order to simulate a natural erection.

In that regard, various surgical implants and implant techniques entail implanting an inflatable bladder in each corpus cavernosum of the penis. A preferred type of penile implant which may be used in combination with the instant invention is disclosed and claimed in my copending U.S. patent application No. 313,114, filed on Oct. 20, 1981, and whose disclosure is incorporated by reference herein.

That implant basically comprises a pair of hollow, enclosed bladders, each having an access port to the interior thereof and formed of a membrane of thin, very flexible material, each of said bladders is capable of inflation by the introduction of a fluid (e.g., water) therein through its port. A respective one of the bladders is located in the passageway in each corpus cavernosum. When the bladders are filled with the fluid, they are inflated from their flaccid state to a third predetermined volume without causing the bladder membrane to undergo tension. The third predetermined volume is sufficiently great to cause the corpra cavernosa to expand so that the fiberous tissue envelope surrounding the corpora cavernosa encompasses the second predetermined volume, whereupon the fiberous tissue becomes tense and the penis becomes hard and erect.

In U.S. Pat. No. 3,954,102 (Buuck) there is disclosed a valve mechanism generally designed to accomplish the inflation and deflation of implanted bladers. The Buuck device comprises means for pumping fluid into the implanted bladders in order to obtain an erection, and valve means for releasing the fluid pressure in order to terminate the erection. With regard to the Buuck device, as well as penile implant systems in general, the resevoir containing the fluid is generally implanted within the patient's lower abdominal cavity. As a result, the patient's internal organs and abdominal wall combine to exert a fairly constant pressure of approximately one pound per square inch upon the walls of the reservoir. The valve system used in Buuck, as well as other prior art penile implant systems, generally fail to provide means for completely withdrawing fluid from the implanted bladders below the residual (e.g., one pound per square inch) level which remains within the bladders during such time that a flaccid state is desired. This residual pressure tends to result not in a flaccid penis but rather, results in a continuously semi-erect one. Moreover, additional fluid tends to build up within the bladders whenever the man coughs or exerts himself in a manner causing increased abdominal pressure to be exerted against the walls of the resevoir. In this regard, when the man coughs or tightens his abdominal muscles during exertion, the pressure on the reservoir increases, thus causing additional fluid to flow into and remain in the bladders. Thus, the bypass valve would have to be actuated periodically to allow the water to run back into the reservoir in order to reduce the pressure within the bladders to the residual level. For this reason, men utilizing prior art implant devices have frequently complained of discomfort associated with being unable to maintain a flaccid state.

Moreover, allowing the bladders, and thus the penis, to remain in a semi-erect state aside from being undesirable from an appearance standpoint can result in either the eventual rupturing of the bladders due to the maintained pressure or an eventual breakdown of the cells surrounding the corpora cavernosa.

OBJECTS OF THE INVENTION

Accordingly, it is a general object of the instant invention to provide a pump and valve assembly which overcomes the disadvantages inherent in the prior art penile implant pump and valve assemblies.

It is another object of the invention to provide a pump and valve assembly which enables a penile implant patient to readily pump fluid into bladders of an implanted prosthesis in order to obtain an erect penis when such is desired and to positively pump the fluid out of the bladders in order to render the penis flaccid.

It is still a further object of the instant invention to provide a pump and valve assembly for use in combination with a penile implant prosthesis which utilizes a manually actuated means to enable one to either pump fluid from a fluid reservoir into implanted bladders or alternatively, pump fluid from the bladders back into the reservoir while positively preventing any return flow or leakage until such time, as would otherwise be desired.

SUMMARY OF THE INVENTION

These and other objects of the instant invention are achieved by providing a pump and valve assembly which is used in combination with a prosthetic penile implant to simulate a natural erection. To that end, the implant includes bladder means which are implanted within the penis and a fluid containing reservoir which is implanted at a remote location thereto. The pump and valve assembly of the instant invention comprises a housing having a first portion which is in fluid communication with the reservoir and a second portion which is in fluid communication with the bladder means. The assembly further comprises uni-directional valve means coupled between the resevoir and the bladder means for controlling the flow of fluid therebetween. Moreover, the assembly also comprises moveable means which when in a first position allows the fluid to flow from the reservoir, through the valve means and into the bladder means and when in a second position allows the fluid to flow from the bladder means, through the valve means and into the reservoir. To that end, the device utilizes means for moving the moveable means either to the first position or to the second position and pumping means which pumps the fluid from the reservoir to the bladder means to produce a simulated erection when the movable means is in the first position and from the bladder means to the reservoir to produce a flaccid penis when the moveable means is in the second positon.

DESCRIPTION OF THE DRAWING

Other objects and many of he attendant advantages of this invention will be readily appreciated as the same becomes better understood by reference to the following detailed description when considered in connection with the accompanying drawing wherein:

FIG. 2a is a similar view as the one of FIG. 2 but during a second mode of operation;

FIG. 3a is a similar view as the one of FIG. 3 but during said second mode of operation;

FIG. 8 is a sectional view taken along line 8—8 of FIG. 7.

DETAILED DESCRIPTION OF THE PREFERRED EMBODIMENT

Figure 1:
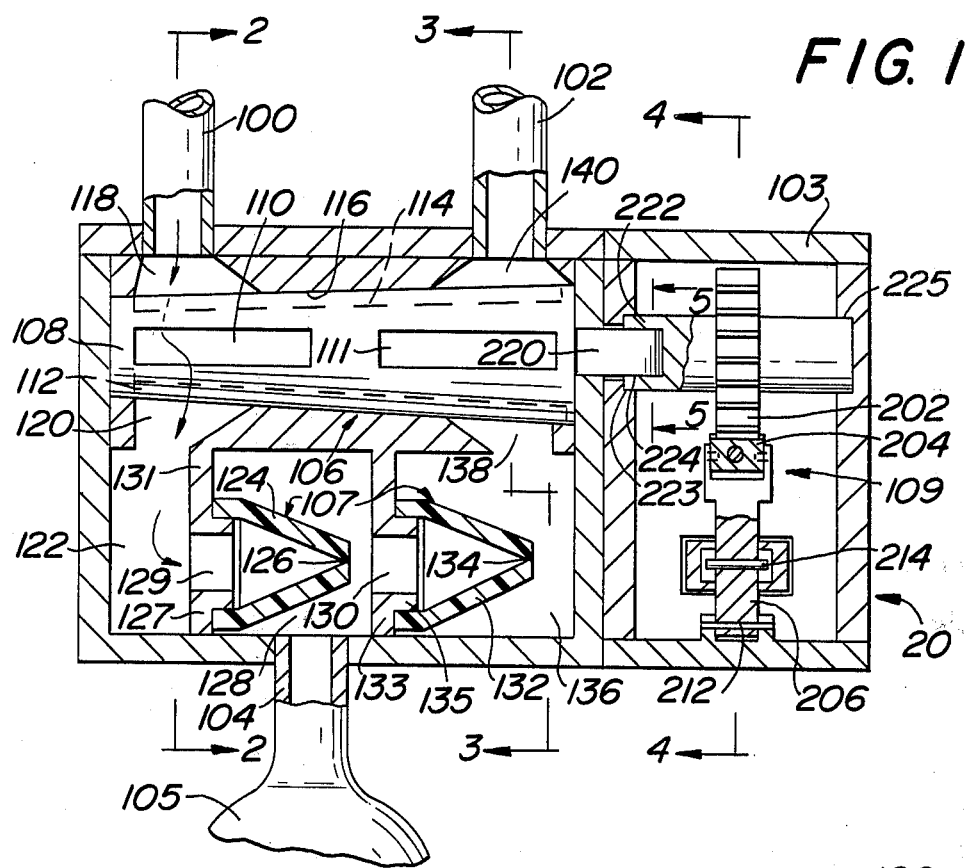
FIG. 1 is a side elevational view partially in section of one embodiment of a pump and valve assembly of the instant invention.

Referring now to the various figures of the drawing wherein like reference characters refer to like parts, there is shown at 20 an implantable pump and valve assembly constructed in accordance with the instant invention and arranged for use in conjunction with inflatable bladder means to form a penile implant. The pump and valve assembly is arranged to be implanted in the body of the patient, connected between the reservoir of water, or other fluid, and the bladders implanted in the corpora cavernosa. The assembly 20 of the instant invention is arranged to positively pump liquid from the reservoir to the bladders to effect the inflation thereof and thereby render the penis erect when such is desired and while precluding any leakage or return flow. Moreover, the assembly is also arranged to enable the bladders to be evacuated by pumping the liquid which is there, out and back to the reservoir when an erection is no longer desired. Assembly 20 basically comprises a first, a second and a third fluid conduit or tube, 100, 102 and 104, respectively, pump means 105 and a housing 103, in which valve means 106 is located. The valve means 106 includes a pair of valve elements, a rotor 108 and selector means 109.

In order to obtain a simulated erection using the instant invention, the rotational means 109 is manually actuated by the selector means as will be discussed later to cause the rotor 108 to rotate from a first radial position to a second one, to allow water to initially flow from the reservoir (not shown) implanted in the abdominal cavity through the tube 100 and into a chamber (to be described later) within the valves' housing. The water then passes through a slot (to be described later) in the rotor 108, through the valve elements 107, through a second slot (to be described later) in the rotor 108, out through the tube 102 and into the bladders (not shown) which are implanted within the corpora cavernosa. The natural pressure applied by the tissue of the abdominal cavity causes the fluid to intially flow as just described. However this natural pressure is insufficient to produce a fully erect penis. Thus, in order to fully erect the penis, the pump means 105 (to be described in detail later) is actuated, that is squeezed manually. This action causes additional fluid to be pumped from the reservoir through the path just described and into the bladders. The number of repetitive pumping actions necessary to effect a full erection is a function of the volumetric capacity of the bladders and the pump means.

To terminate the erection, the selector means 109 is again manually actuated causing the rotor 108 to rotate back to said first radial position, thus, allowing fluid contained within the bladders to pass through tube 102, along a recess (to be described later) in the rotor 108, through valve means 107, through a second recess in the rotor 108, through the tube 100 and back into the reservoir under the pressure produced by the abdominal cavity. The return flow caused by the natural pressure applied by the bodily tissues to the implant allows only a partial return of the liquid to the reservoir, since such flow ceases when the pressure is equalized in the system, that is the pressure in the bladders is the same as the pressure in the reservoir. Accordingly, at this point the penis is semi-erect. In order to obtain a fully flaccid penis additional fluid is pumped out of the bladders by means of repeated actuation of the pump means 105 to force additional fluid to pass from the bladders into the reservoir.

In a preferred implementation of the embodiment shown in FIG. 1, the pump and valve assembly 20 is arranged to be surgically implanted within a patient's scrotum while the reservoir (not shown) is implanted within the patient's lower abdominal cavity.

The pumping action just described is achieved by manually squeezing the pump means 105 through the skin of the scrotum, whereupon fluid from either the reservoir or the bladders is pumped either from the reservoir to the bladders or from the bladders to the reservoir, respectively, depending on the rotational position of the rotor 108.

The operation of the pump and valve assembly shall now be described in detail. In order to obtain an erection (i.e., to fill the bladders with fluid), the selector means 109 is manually actuated (as shall be described later) to cause the rotor 108 to rotate to the rotational position shown in FIGS. 1, 2 and 3.

The rotor 108 is a generally cylindrical, frusto conical member situated within a bore 116 in the housing 103 and comprises a pair of generally rectangular slots 110 and 111, respectively, extending diametrically through the rotor 108. The slots are coplanar but located a different longitudinal positions along the rotor 108. The rotor 108 also comprises a pair of enlongated recesses 112 and 114. To that end, recess 112 extends longitudinally down the surface of the rotor 108 at a radial position approximately 90° from the plane of the slots 110 and 112. The recess 114 is constructed similar to recess 112 and is located diametrically opposite thereto. Each recess 112 and 114 extends for substantially the entire length of the rotor 108.

All of the recesses and all of the slots are isolated from one another. Since the reservoir is under a more or less constant abdominal pressure, when the rotor 108 is rotated to the position shown in FIGS. 1, 2, and 3 the water contained therein flows in the direction of the arrows through tube 100 and into chamber 118 within the housing 106. The fluid then passes from the chamber 118, through the slot 110 in the rotor, into an upper port area 120 of a chamber 122.

Contiguous with the chamber 122 is one of the valve elements 107. Element 107 comprises check valve 124 formed of a resilient material and which enables water to flow in only one direction therethrough. Thus, communication between the chamber 122 and another chamber 128 is established, with the direction of the communication being from left to right as shown in FIG. 1. As can be seen, the check valve 124 is of the "Duck Bill" type having a generally conically shaped member with an outlet slit 126 at the apex thereof. The member 124 is secured on a flange 127 extending about a port 129 in a wall 131. The wall 131 separates chamber 122 from a second chamber 128 and to which the outlet slit 126 of the check valve 124 is in communication. The tube 104, which is in fluid communication with the pump means 105 is in fluid communication with the chamber 128.

As will be appreciated by those skilled in the art, with the arrangement just described fluid is able to pass from chamber 122 into chamber 128 while fluid within chamber 128 is precluded from passing in the reverse direction from chamber 128 into chamber 122. Chamber 128 is also in fluid communication with the pump means 105 by means of the tube 104. In addition, chamber 128 is contiguous to an opening 130 in a wall similar to wall 133.

The second of the valve elements 107 is in the form of check valve 132. Check valve 132 is identical to check valve 124 and is mounted on a flange 135 on the wall 133 and extends about opening 130. The outlet slit 134 of check valve 132 is in communication with another chamber 136. Thus, valve 132 acts to permit fluid to pass from intermediate chamber 128 into chamber 136 while at the same time precluding fluid from passing in the reverse direction.

Figure 2:
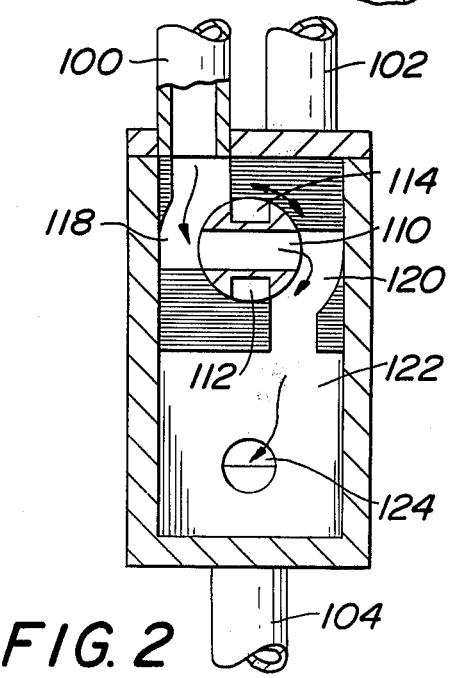
FIG. 2 is a sectional view taken along line 2—2 of FIG. 1 during one mode of operation.
Figure 3:
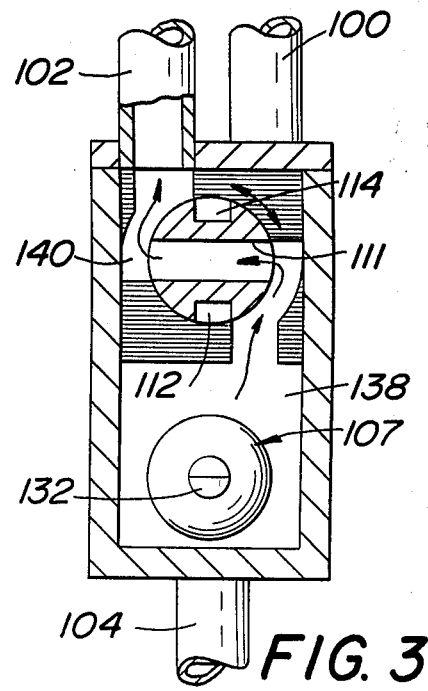
FIG. 3 is a sectional view taken along line 3—3 of FIG. 1 during said one mode of operation.

When the rotor is in the position as shown in FIGS. 1, 2 and 3 water within chamber 136 is enabled to flow through an outlet port 138 at the top of chamber 136, through slot 111 in the rotor and into a passageway 140 at the top of the housing contiguous with the tube 102. Thus, the water is enabled to flow into tube 102 and to the bladders within the penis.

When the rotor is first positioned as shown in FIGS. 1, 2, and 3 the water naturally begins to flow from the reservoir through the valve assembly in the path just described and to the bladders under the ambiant body pressure exerted on the reservoir. Once pressure equilibrium is reached, that is the pressure produced by the body on the reservoir is equal to the pressure on the bladders within the penis, no further water flow into the bladders of the penis occurs and the penis will thus only be semi-erect.

The pump mechanism of the instant invention accomplishes the further filling of the bladders through the valve system. To that end the pump 105 basically comprises a hollow, bulb-like member, formed of a resilient material, and arranged to be squeezed manually. Since the bulb 105 is in fluid communication with the chamber 128, via tube 104, the squeezing of the bulb causes water within chamber 128 to flow through the check valve 134 into chamber 136 and through the connecting fluid path through the bladders. In addition the pumping action reduces the pressure within chamber 128 as compared to chamber 122, thereby drawing additional water from the reservoir, through a tube 100 into the chamber 122 and then into the chamber 128. Thus, by repeated squeezing of the bulb 105 sufficient water can be pumped from the reservoir into the bladders to effect the attainment of the viable erection.

As should readily be appreciated from the foregoing discussion, fluid pumped from the reservoir into the bladders is precluded from flowing back to the reservoir by the action of the uni-directional valves 124 and 132.

In order to terminate the erection (i.e., move the water out of the bladders and back into the reservoir), the selector mean 109 is actuated to cause the rotor 108, to rotate 90° about its longitudinal axis to the position shown in FIGS. 2A and 3A. As can be seen therein, rotation of the rotor 108 to that orientation places the recess 112 in communication with both passageway 140 (FIG. 3A) and the upper port 120 (FIG. 2A), thus interconnecting them. As a result, water immediately begins to flow from the tube 102, down the recess 112 and into chamber 122. The water then passes through the valve 124 and into the chamber 128. The water flows from chamber 128, through the valve 132, into chamber 136 and into passageway 138 (FIG. 3A). The water then flows down the second recess 114 into the chamber 118 (FIG. 2A), and then into the reservoir by means of the tube 100. Such flow occurs notwithstanding any pumping action, until the point is reached in which the pressure throughout the system has been equalized. As should readily be appreciated, this results in only a partial emptying of the bladders and a partial refilling of the reservoir. As a result, the penis does not return to a flaccid state but remains semi-rigid.

In order to make the penis a flaccid the bulb is squeezed manually to pump additional water from the bladders, into the reservoir in the same manner as used to create the erection.

Figure 4:
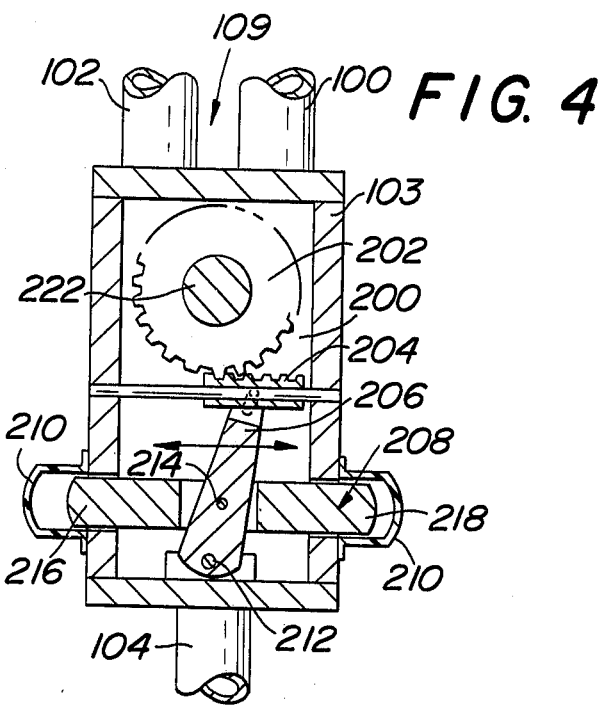
FIG. 4 is a sectional view taken along line 4—4 of FIG. 1.
Figure 5:
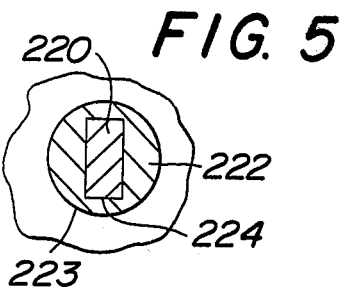
FIG. 5 is a sectional view taken along line 5—5 of FIG. 1.

The selector means 109 is shown clearly in FIGS. 1 and 4 and serves as the means for rotating the rotor 108 in order to select the desired mode of operation (i.e., inflation or deflation).

The selector means 109 comprises a gear assembly also mounted within the housing 106. To that end, the gear assembly 200 includes a gear 202, a rack 204, a pivot arm 206 and a bi-directional push/pull slider 208. The slider is arranged to be reciprocated back and forth. Each of the ends 216 and 218 of the slider 208 is covered with a resilient cap 210 secured to the housing to enable the slider to be reciprocated manually by the application of manual pressure thereon.

The pivot arm 206 is at one end pivotably connected to the housing 106 by means of a pivot pin 212 and is connected at an intermediate location to the slide 208 by means of a second pivot pin 214. The other end (i.e., the free end) of the arm 206 is connected to the rack 204. Thus, the arm 206 pivots about pin 212 in either the clockwise or counter clockwise direction (as shown by the arrows in FIG. 4) to slide the rack 204.

Figure 6:
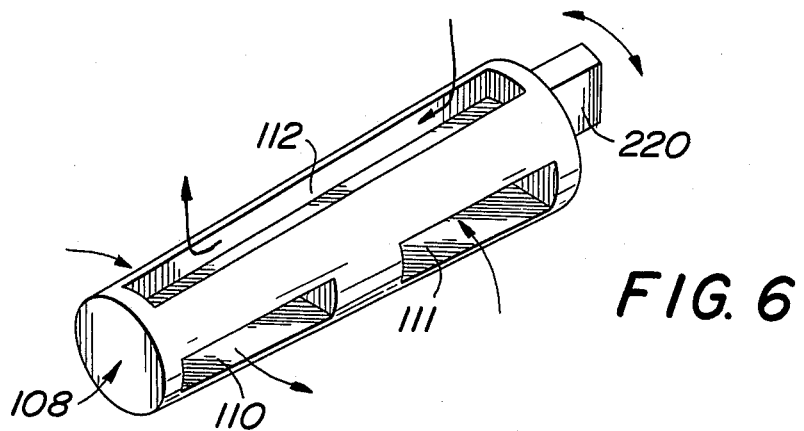
FIG. 6 is an enlarged perspective view of a rotor, a portion of the pump and valve assembly shown in FIG. 1.

This action causes the mating gear to rotate either clockwise or counter clockwise. The gear is mounted on a shaft 222 in the housing and includes a slot 224 into which a key 220 (FIG. 6) of the rotor 108 is located. The key extends through an opening in a wall of the housing 103 separating the valve assembly from the selector means.

Thus, as readily can be appreciated from the foregoing, by pushing on end 216 one moves the slider from left to right in FIG. 4 whereupon the gear and connected rotor rotate in the counter clockwise direction. Conversely, pushing end 218 effects clockwise rotation of the rotor. Thus the rotor can be moved to either the position shown in FIGS. 2 and 3 or FIGS. 2A and 3A by appropriate actuation of the slide.

Since the pump-valve assembly of FIG. 1 is preferably inplanted in the scrotum actuation of the slider can be readily effected through the thin tissue thereof.

Figure 7:
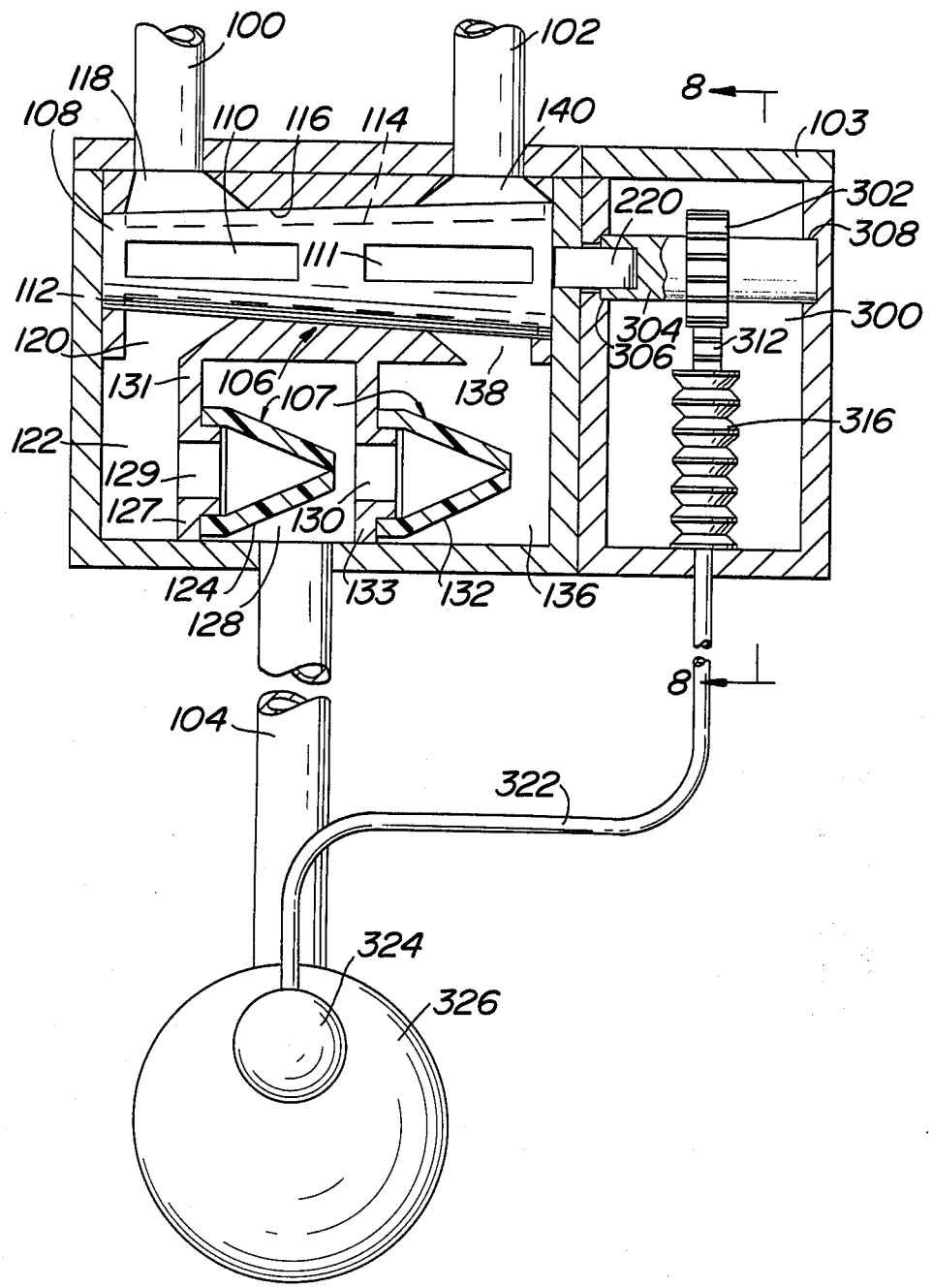
FIG. 7 is a side elevational view, of an alternative embodiment of the pump and valve assembly of the instant invention.

An alternative and preferred embodiment of the invention, as shown in FIG. 7, enables the assembly 20 to be implanted at some non-gential area location within the man's body (e.g., within the abdominal cavity) in lieu of scrotum implantation.

The advantage of the embodiment of FIG. 7 is that by implanting the valve within the abdominal cavity or at other some remote location more space is available in the scrotum to accommodate a larger capacity bulb 105. As will be readily understood by those skilled in the art, the use of a larger capacity bulb is desirable in that it can materially lessen the number of pump squeezes necessary to effect inflation or deflation.

In the embodiment of FIG. 7, the bulk of the selector means for effecting rotation of the rotor is located within the housing in which the valve assembly is located except for a pair of actuators, to be described hereinafter, which are located with the pump bulb within the scrotum.

As can be seen in FIG. 7 the valve means 106 is constructed in essentially the identical manner as that described with reference to the embodiment shown in FIG. 1. Moreover, the tubes 100 and 102 are connected in identical manner as described with reference to FIG. 1. The tube 104 in the embodiment shown in FIG. 7 constitutes an elongated tube which extends from the housing implanted within the abdominal cavity to the pump means (to be described later) implanted within the scrotum. The selector means of FIG. 7 is constructed differently than that of FIG. 1. In this regard, the selector means of FIG. 7 comprise an assembly 300 housed within the housing 103. The selector means 300 includes a gear 302 mounted on a hub or shaft 304 and connected to the key 220 in a manner as described with reference to FIG. 1. The gear is arranged to be rotated either clockwise or counter clockwise to effect rotation of the rotor by a pair of racks 310 and 312. Each rack has associated therewith a respective, expandable bellows. To that end, rack 312 is mounted on the upper end of bellows 316 while rack 310 is mounted on the upper end of bellows 314. The racks and associated bellows are mounted within the housing on opposite sides of the gear so that rack 312 engages gear 302 on one side thereof while rack 310 engages the gear on the diametrically opposed side thereof.

The respective racks are arranged to reciprocate vertically responsive to the action of the bellows. In paricular, when bellows 314 expands, rack 310 moves up while rack 312 moves down, thus compressing bellows 316. When bellows 316 expands rack 312 moves up, thereby compressing bellows 314.

As can be seen in FIG. 8, the bellows 314 communicates with a fluid line 318 which is connected to a hollow actuator bulb 320. Likewise, bellows 316 communicates through a fluid line 322 with a second actuator bulb 324. Both actuator bulbs are implanted adjacent the valve's pump 326 within the scrotum. Thus, when the actuator bulb 320 is squeezed, water contained therein is forced up through line 318 into bellows 314, thus extending the bellows and associated rack 310 (as shown in FIG. 8). This causes gear 302, to rotate in a counter clockwise direction which in turn pushes rack 312 downward, thus compressing the bellows 316 and forcing the water contained within the bellows 316 through the tube 322 and back into the actuator bulb 324.

Each actuation bulb and its associated bellows is a sealed hydraulic system so that actuation of either causes the gear to rotate in the associated direction and to remain in that orientation until rotated back by the actuation of the other actuator bulb. The volumetric capacity of each bellows is small yet is capable of a long linear expansion. Thus, small volumetric capacity actuation bulbs can be utilized to effect expansion of the associated bellows and rotation of gear 302 while providing greater room within the scrotum to accomodate the pump 326 for inflating and deflating the implanted bladders.

The pump 326 for the pump-valve assembly of the embodiment of FIG. 7 is constructed similarly to pump bulb 105 except that the latter has a substantially greater volumetric capacity. Thus, fewer depressions of the pump 326 are necessary in order to either inflate or deflate the bladders.

As will be appreciated from the foregoing, the pump and valve assembly 20 of the instant invention is relatively simple in construction and is a highly effective means for either inflating or deflating a penile implant to produce either a simulated erection or a flaccid penis, respectively, as desired.

Without further elaboration the foregoing will so fully illustrate my invention that others may by applying current or future knowledge readily adapt the same for use under various conditions of service.

I claim:

1. For simulating a natural erection, a pump and valve assembly to be used in combination with a prosthetic penile implant which includes bladder means which are implanted within the penis and a fluid containing reservoir which is implanted at a remote location thereto, wherein said assembly comprises a housing, a first portion of which is in fluid communication with said reservoir and a second portion of which is in fluid communication with said bladder means, valve means coupled between said reservoir and said bladder means for controlling the flow of fluid therebetween, moveable means which when in a first position allows said fluid to flow from said reservoir, through said valve means into said bladder means and when in a second position allows said fluid to flow from said bladder means, through said valve means and into said reservoir, means for moving said moveable means between said first and second positions, pump means coupled to said valve means for pumping said fluid from said reservoir to said bladder means to produce a simulated erection when said moveable means is in said first position and from said bladder means to said reservoir to produce a flaccid penis when said moveable means is in said second position.

2. The assembly of claim 1, wherein said pump means comprises a generally hollow bulb.

3. The device of claim 2, wherein said moveable means comprises rotor means.

4. The assembly of claim 1, wherein said valve means comprises a first valve and a second valve which are housed within a first valve chamber and a second valve chamber, respectively, such that said first valve and said second valve are connected to each other in series, such that fluid passes through said first valve in order to enter said first valve chamber and passes through said second valve to exit said first valve chamber and enter said second valve chamber.

5. The assembly of claim 4, wherein said rotor means comprises slot means and recess means situated at different radial positions along said rotor means such that when said rotor means is in said first position fluid passes from said reservoir to said bladder means by passing through said slot means and when said rotor is in said second position fluid passes from said bladder means to said reservoir by passing along said recess means.

6. The device of claim 5, wherein said slot means comprises a first and a second slot and said recess means comprises a first and a second recess, such that the fluid passing from said reservoir to said bladder means flows through said first slot, through said first valve, into said first valve chamber, through said second valve, into said second valve chamber, through said second slot and into said bladder while fluid flowing from said bladder means to said reservoir flows along said first recess, through said first valve, into said first valve chamber, through said second valve, into said second valve chamber, through said second recess and into said reservoir.

7. The assembly of claim 6, wherein said rotor means is a generally cylindrical, frusto conical member with said slots and said recesses being longitudinally disposed along the curved surface of said rotor means such that said slots are disposed at a generally 90° angle relative to said recesses and each of said recesses are disposed along diametrically opposite portions of said surface.

8. The device of claim 4, wherein said pump means is connnected in fluid communication with said first valve chamber such that the pumping action of said pump means draws fluid through said first valve into said first valve chamber as well as causes fluid to flow from said first valve chamber through said second valve and into said second valve chamber, whereupon said fluid passes to either said bladder means or to said reservoir depending on whether said rotor means is in said first position or in said second position, respectively.

9. The device of claim 3, wherein said rotational means comprises a manually actuated slide member coupled to a gear assembly which rotates said rotor means to either said first position or to said second position, respectively.

10. The device of claim 9, wherein said gear assembly comprises a generally circular gear, a corresponding toothed rack and a pivot arm such that the sliding of said slide member causes said pivot arm to rotate, thus causing said gear to rotate.

11. The device of claim 2 wherein said pump means is located remote from said housing and wherein said moveable means is coupled to actuating means located remote from said housing.

12. The device of claim 11 wherein said moveable means comprises rotor means.

13. The device of claim 12, wherein said actuating means comprises an actuating pump coupled to a bellows located within said housing such that when said actuating pump is squeezed said bellows expands causing said rotor means to rotate between said first and second positions and vice versa.

14. The device of claim 11, additionally comprising a gear which is coupled to said rotor means and a rack, such that the expansion of said bellows causes said rack to move in a first direction, thus rotating said gear in a first radial direction, while the contraction of said bellows causes said rack to move in a second direction, thus causing said gear to rotate in the opposite radial direction.

15. The device of claim 14, further comprising a second actuating pump, second bellows, a second gear, and a second rack all coupled to said rotor means, such that when said first actuating pump is squeezed said rotor means rotates in said first radial direction to a first radial position and when said second actuating pump is squeezed said rotor rotates in said opposite radial direction to a second radial postion.

16. The device of claim 15, wherein said valve means comprises a first valve and a second valve which are housed within a first valve chamber and a second valve chamber, respectively, such that said first valve and said second valve are connected to each other in series, such that fluid passes through said first valve in order to enter said first valve chamber and passes through said second valve to exit said first valve chamber and enter said second valve chamber.

17. The device of claim 16, wherein said rotor means comprises slot means and recess means situated at different radial positions along said rotor means such that when said rotor means is in said first position fluid passes from said reservoir to said bladder means by passing through said slot means and when said rotor is in said second position fluid passes from said bladder means to said reservoir by passing along said recess means.

18. The device of claim 17, wherein said slot means comprises a first and a second slot and said recess means comprises a first and a second recess, such that the fluid passing from said reservoir to said bladder means flows through said first slot, through said first valve, into said first valve chamber, through said second valve, into said second valve chamber, through said second slot and into said bladder while fluid flowing from said bladder means to said reservoir flows along said first recess, through said first valve, into said first valve chamber, through said second valve, into said second valve chamber, through said second recess and into said reservoir.

19. The device of claim 18, wherein said rotor means is a generally cylindrical, frusto conical member with said slots and said recesses being longitudinally disposed along the curved surface of said rotor means such that said slots are disposed at a generally 90° angle relative to said recesses and each of said recesses are disposed along diametrically opposite portions of said surface.

20. The device of claim 19, wherein said pump means is connected in fluid communication with said first valve chamber such that the pumping action of said pump means draws fluid through said first valve into said first valve chamber as well as causes fluid to flow from said first valve chamber through said second valve and into said second valve chamber, whereupon said fluid passes to either said bladder means or to said reservoir depending on whether said rotor means is in said first position or in said second position, respectively.

* * * * *